United States Patent
Franke et al.

[11] Patent Number: 5,326,707
[45] Date of Patent: Jul. 5, 1994

[54] COMPOSITION AND DEVICE FOR URINARY PROTEIN ASSAY AND METHOD OF USING THE SAME

[75] Inventors: Gunter Franke, Leichlingen, Fed. Rep. of Germany; Michael Salvati, St. Paul, Minn.; Ronald G. Sommer, Elkhart, Ind.

[73] Assignee: Miles Inc., Elkhart, Ind.

[21] Appl. No.: 800,272

[22] Filed: Nov. 29, 1991

[51] Int. Cl.$^5$ ............................................. G01N 33/00
[52] U.S. Cl. ...................................... 436/86; 436/87; 436/88; 422/56; 252/408.1
[58] Field of Search ............... 436/86, 87, 88; 422/55, 422/56, 57, 408.1; 252/408.1

[56] References Cited

U.S. PATENT DOCUMENTS

| | | | |
|---|---|---|---|
| 4,013,416 | 3/1977 | Rittersdorf et al. | 436/86 |
| 5,013,527 | 5/1991 | Arai et al. | 422/58 |
| 5,049,358 | 9/1991 | Lau | 436/86 |
| 5,096,833 | 3/1992 | Lau et al. | 436/86 |
| 5,124,266 | 6/1992 | Coryn et al. | 436/88 |
| 5,187,104 | 2/1993 | Corey et al. | 436/86 |

*Primary Examiner*—James C. Housel
*Assistant Examiner*—Lien Tran
*Attorney, Agent, or Firm*—Roger N. Coe

[57] ABSTRACT

A composition, test device and method of determining the presence or concentration of proteins, such as albumin, in a liquid test sample, such as urine. The test device includes a test pad with a carrier matrix incorporating a indicator reagent composition capable of interacting with proteins to produce a detectable response. The indicator reagent composition includes an indicator dye that is capable of interacting with albumin and undergoing a detectable color transition; a buffer; a hydrophobic polymeric compound having the general structural formula:

$$H + A - R_1 \to_n A - E, \qquad (I)$$

wherein A is

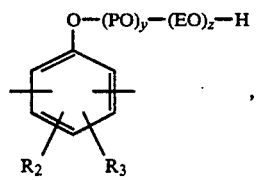

and PO is an oxypropylene unit, EO is an oxyethylene unit, y is a number in the range of 0 to about 20, z is a number in the range of 0 to about 20, the sum y+z is a number in the range of about 2 to about 20, and $R_2$ and $R_3$ are selected, independently, from the group consisting of hydrogen, an alkyl group, an aralkyl group, and an aryl group;

$R_1$ is either methylene or oxygen;

n is a number in the range of one to about 8; and

E is hydrogen or methylol when $R_1$ is methylene, or E is hydroxy when $R_1$ is oxygen; and a suitable carrier which is water. The indicator reagent composition provides an improved color resolution in the test samples raving negative protein and trace amount of protein.

28 Claims, 1 Drawing Sheet

EFFECT OF POLYMER II ON TBPB STRIPS
HSA dose response in urine (SG=1.007)

FIGURE 1

EFFECT OF POLYMER II ON TBPB STRIPS
HSA dose response in urine (SG=1.007)

COMPOSITION AND DEVICE FOR URINARY PROTEIN ASSAY AND METHOD OF USING THE SAME

FIELD OF THE INVENTION

The present invention relates to an improved composition, assay device and method of assaying a test sample for the presence or concentration of protein. More particularly, the present invention relates to a composition, method and device for assaying a liquid test sample, such as urine, for proteins, and especially for negative and trace amounts of proteins, by utilizing a test device including a test pad comprising a new and improved indicator reagent composition incorporated into a carrier matrix, wherein a detectable or measurable response occurs upon contact of the test pad with a protein-containing liquid. The new and improved indicator reagent composition comprises: (1) an indicator dye that is capable of interacting with albumin and undergoing a detectable response, such as a color transition; (2) a buffer; and (3) a hydrophobic polymeric compound having the general structural formula (I):

wherein A is and PO is an oxypropylene unit, EO is an oxyethylene unit, y is a number in the range of 0 to about 20, z is a number in the range of 0 to about 20, the sum y+z is a number in the range of about 2 to about 20, and $R_2$ and $R_3$ are selected, independently, from the group consisting of hydrogen, an alkyl group, an aralkyl group, and an aryl group;

$R_1$ is either methylene or oxygen;

n is a number in the range of one to about 8; and

E is hydrogen or methylol when $R_1$ is methylene, or E is hydroxy when $R_1$ is oxygen.

The new indicator reagent composition provides an improved color resolution in the test pad, and therefore an improved color differentiation between test samples assayed as including a negative amount of protein and test samples assayed as including a trace amount of protein. Accordingly, the number of false positive assays for protein is substantially reduced. By substantially reducing the number of false positive assays for albumin, fewer unnecessary confirmatory assays to verify the presence of a trace amount of protein in a test sample are performed. In addition, the present invention relates to incorporating the new indicator reagent composition into a carrier matrix to provide a test pad of a test device in an improved method to determine the presence or concentration of proteins, like albumin, in a test sample by a dry phase, test strip assay procedure.

BACKGROUND OF THE INVENTION AND PRIOR ART

Albumin is the most abundant plasma protein, generally constituting slightly over one-half of the total protein in mammalian plasma. In the human body, albumin has the important role of regulating the water balance between blood and tissues, and of functioning as a transport molecule for various compounds, such as bilirubin, fatty acids, cortisol, thyroxine and drugs like sulfonamides and barbiturates, that are only sparsely soluble in water. An albumin deficiency can restrict the transport of sparsely water soluble materials throughout the body and a deficiency is signaled in an individual by an abnormal accumulation of serous fluid, or edema. Therefore, it is clinically important to determine whether an individual has a deficiency of serum albumin.

Likewise, it is clinically important to determine if an individual is excreting an excess amount of protein. A normal functioning kidney forms urine in an essentially two step process. Blood flows through the glomerulus, or glomerular region of the kidney. The capillary walls of the glomerulus are highly permeable to water and low molecular weight components of the blood plasma. Albumin and other high molecular weight proteins cannot pass through these capillary walls and essentially are filtered out of the urine so that the protein is available for use by the body. The liquid containing the low molecular weight components passes into the tubules, or tubular region, of the kidney where reabsorption of some urine components, such as low molecular weight proteins; secretion of other urine components; and concentration of the urine occurs. AM a result, through the combined processes of the glomerulus and tubules, the concentration of proteins in urine should be minimal. Therefore, abnormally high amounts of albumin in urine must be detected and related to a physiological dysfunction.

A relatively high concentration of albumin in the urine of an individual usually is indicative of a diseased condition. For example, the average normal concentration of protein in urine varies from about 10 mg/dL (milligrams per deciliter) to about 20 mg/dL, with approximately one-fifth of the total urinary protein being serum albumin. However, in a majority of diseased states, urinary protein levels increase appreciably, such that albumin accounts for from about 60 percent to about 90 percent of the excreted protein. The presence of an abnormal increased amount of protein in the urine, known as proteinuria, is one of the most significant indicators of renal disease, and may be indicative of various other non-renal related diseases.

Therefore, in order to determine if an individual has an albumin deficiency or to determine if an individual excretes an excess amount of protein, and in order to monitor the course of medical treatment to determine the effectiveness of the treatment, simple, accurate and inexpensive protein detection assays have been developed. Furthermore, of the several different assay methods developed for the detection or measurement of protein in urine and serum, the methods based on dye binding techniques have proven especially useful because dye binding methods are readily automated and provide reproducible and accurate results.

In general, dye binding techniques utilize pH indicator dyes that are capable of interacting with a protein, such as albumin, and that are capable of changing color upon interaction with a protein absent any change in pH. When a pH indicator dye interacts with, or binds to, a protein, the apparent $pK_a$ (acid dissociation constant) of the indicator dye is altered and the dye undergoes a color transition, producing the so-called "protein-error" phenomenon. In methods utilizing the dye binding technique, an appropriate buffer maintains the pH indicator dye at a constant pH to prevent a color transition of the pH indicator dye due to a substantial shift in pH. Due to the "protein-error" phenomena, the pH indicator dye undergoes a color transition upon interaction with protein that is identical to the color change arising because of a change in the pH. Examples of pH indicator dyes used in the dry phase assay of proteins that are capable of interacting with or binding to proteins and exhibiting "protein-error" color transitions include tetrabromophenol blue (TBPB) and tetrachlorophenol-3,4,5,6-tetrabromosulfophthalein.

Although pH indicator dyes have been used extensively in protein assays, several disadvantages still exist in protein assay methods utilizing indicator dyes. For example, methods based upon pH indicator dyes cannot sufficiently differentiate, quantitatively, between a trace protein concentration of about 15 to about 30 mg/dL and a negative protein concentration below about 15 mg/dL. A negative protein concentration is the normal background amount of protein present in urine, and is clinically insignificant. A trace protein concentration shows a slightly elevated amount of protein in urine and is clinically significant. An assay showing a trace amount of protein requires a confirmatory assay to conclusively show that an elevated amount of protein is present in the urine. Although several simple quantitative assays are available for the determination of the total protein content in a test sample, the majority of these assay methods, with the notable exception of the simple colorimetric reagent test strip, require the precipitation of protein to make quantitative protein determinations. Accordingly, the confirmatory assays are more time consuming and expensive than the test strip assays used to screen the urine samples for protein content. Therefore, a need exists for a test strip assay that substantially reduces the number of false positive assays for a trace amount of protein.

The colorimetric reagent test strip utilizes the previously discussed ability of proteins to interact with certain acid-base indicators and to alter the color of the indicator without any change in the pH. For example, when the indicator tetrabromophenol blue (TBPB) is buffered to maintain a constant pH of approximately 3, the test pad remains a yellow color upon contact with a test sample that does not contain protein. However, for test samples containing protein, the presence of protein causes the buffered dye to impart either a greenish-yellow color, a green color or a blue color to the test pad, depending upon the concentration of protein in the test sample. Consequently, the development of a greenish-yellow color in the test pad of a dry phase test strip can be interpreted as a trace amount of protein or as a negative amount of protein.

Some colorimetric test strips used in protein assays have a single test area consisting of a small square pad of a carrier matrix impregnated with a buffered pH indicator dye, such as tetrabromophenol blue. Other colorimetric test strips are multideterminant reagent strips that include one test area, or test pad, for the protein assay as described above, and further include several additional test pads on the same strip to permit the simultaneous assay of other urinary constituents, like pH. For both types of colorimetric test strips, the assay for protein in urine is performed simply by dipping the colorimetric test strip into a well mixed, uncentrifuged urine sample, then comparing the resulting color of the test pad of the test strip to a standardized color chart provided on the colorimetric test strip bottle.

For test strips utilizing tetrabromophenol blue, buffered at pH 3, as the indicator dye, quantitative assays for protein can be performed and are reported as negative, trace, or one "plus" to four "plus". A negative reading, or yellow color, indicates that the urine contains less than about 15 mg/dL protein, as demonstrated by the lack of a color transition of the indicator dye. A trace reading, or greenish-yellow color, indicates that the urine contains from about 15 to about 30 mg/dL of protein. The one "plus" to four "plus" readings, signified by color transitions of green through increasingly dark shades of blue, are approximately equivalent to urine protein concentrations of 30, 100, 300, and over 2000 mg/dL protein, respectively, and serve as reliable indicators of increasingly severe proteinuria. Therefore, differentiating between a negative assay (yellow color) and a trace assay (greenish-yellow color) is important for an accurate protein analysis.

In accordance with the above-described method, an individual can readily determine, visually, that the protein content of a urine sample is in the range of 0 mg/dL to about 30 mg/dL. However, the color differentiation afforded by the presently available commercial test strips is insufficient to allow an accurate determination of urinary protein content between a sample having less than about 15 mg/dL protein (negative) and a sample including from about 15 to about 30 mg/dL protein (trace). The inability to differentiate between low urinary protein concentrations is important clinically because a healthy person usually has a urine protein level in the range of about 2 mg/dL to about 20 mg/dL. Therefore, it is clinically important to determine precisely the urine protein content of an individual, rather than merely estimating the protein content at some value less than about 30 mg/dL.

A trace reading for urinary protein is considered a positive assay, and confirmation of a positive test strip reading is required. The prevalent method of confirming a test strip positive protein assay is the turbidimetric sulfosalicylic acid method, abbreviated as SSA. A high frequency of false positive assays, requires confirmatory testing for each false positive assay, and the attendant added cost. Therefore, it is important that a screening test for protein, like a test strip assay, provide a low frequency of false positive readings.

Trace proteinuria is defined as protein excretion slightly above normal proteinuria. Normal excretion of protein is 50–150 mg/24 hours and 200–300 mg/24 hours in pregnancy. Using an average urine volume of 1250 mL/24 hrs, concentration units of 4–12 mg/dL (16–20 mg/dL in pregnancy) are calculated. Since 24 hour urine volumes vary from about 700 mL to more than 2000 mL, the range of normal protein is considerably wider, and, as expected, the more concentrated urine samples of higher specific gravity (SG) contain more protein. Trace proteinuria, then, is the concentration of protein that falls between negative and one "plus" (30 mg/dL). However, since normal proteinuria covers a range of protein concentrations, trace proteinuria also covers a range of protein concentrations. The trace protein concentration also is dependent on the specific gravity, or SG, of the sample.

The variation of protein concentration with SG does not effect the confirmatory SSA assay, and therefor protein precipitation in the SSA assay is considered indicative of clinical proteinuria. However, the SSA method also has limitations because it is a qualitative method and because procedures vary between clinical laboratories. Accordingly, the problem with a trace reading for protein provided by a screening test, such as a dry phase test strip, is that the reading must correspond to a protein range that is not well defined for clinical samples; that is dependent on the SG of the sample; and that overlaps with the normal, or negative, protein range. Further, trace readings are usually confirmed as positive by a qualitative method that has not been standardized, but is the method of choice in the art because the method is easy, requires no instrumentation, and detects clinical proteinuria in the presence of normal protein.

Of course, the protein content of a urine sample can be determined more precisely by quantitative 24 hour protein precipitation techniques. However, these tests are time consuming and relatively expensive. Furthermore, the precipitation tests must be run in a laboratory by trained personnel, and therefore are unavailable for the patient to perform at home to quickly determine urine protein content and to monitor the success or failure of a particular medical treatment.

Therefore, it would be extremely advantageous to have a simple, accurate and trustworthy method of assaying urine for protein content that allows visual differentiation of protein levels in the ranges of 0 mg/dL to about 15 mg/dL and about 15 mg/dL to about 30 mg/dL, and upwards to between about 100 mg/dL to about 300 mg/dL. By providing such an accurate method of determining urine protein concentration in an easy to use form, such as a dip-and-read test strip, the urine assay can be performed by laboratory personnel to afford immediate test results, such that a diagnosis can be made without having to wait up to one day for assay results and medical treatment can be commenced immediately. In addition, the test strip method can be performed by the patient at home to more precisely monitor low levels of protein in urine and monitor the success of the medical treatment the patient is undergoing, without providing a large number of false positive assays that require unnecessary, time consuming and costly confirmatory testing. Finally, the method and composition used in a protein assay should be independent of the specific gravity of the urine to provide an accurate protein assay.

For example, the current urinary protein reagent test strips contain an octahalosulfophthalein protein indicator, e.g., tetrabromophenol blue (TBPB), as the indicator dye. When these strips are dipped into albumin-free urine samples of low to medium specific gravity, e.g., SG less than 1,020, the strips turn to a yellowish-green color. When the same strips are dipped into an albumin-free, high SG urine sample, e.g., SG equal to or greater than 1,020, the strips turn to a greenish-yellow color. This greenish-yellow color easily can be interpreted incorrectly as a clinically significant trace concentration of albumin (10–15 mg/dL). However, even with low SG urine samples, the negative color is difficult to differentiate from a true trace color.

As will be described more fully hereinafter, the method of the present invention allows the fast, accurate and trustworthy protein assay of urine by utilizing a test strip that includes a test pad comprising a carrier matrix incorporating a new and improved indicator reagent composition. Surprisingly and unexpectedly, the indicator reagent composition of the present invention essentially eliminates the interfering effects of specific gravity on the assay of urine samples including negative to trace amounts of protein. The new and improved indicator reagent composition of the present invention enhances visual color resolution by essentially eliminating the development of an interfering greenish-yellow color by high SG test samples including a negative amount of albumin. Therefore the sensitivity of the assay is enhanced, allowing urine protein concentrations to be determined accurately at levels of about 30 mg/dL or less, and precluding costly confirmatory testing arising from a false positive screening assay for albumin. In addition, the method of the present invention also can be used to determine the presence or concentration of higher concentrations of proteins, such as from about 100 mg/dL to about 2000 mg/dL, in a test sample.

Proteinuria resulting from abnormally high albumin levels depends upon the precise nature of the clinical and pathological disorder and upon the severity of the specific disease. Proteinuria can be intermittent or continuous, with transient, intermittent proteinuria usually being caused by physiological or functional conditions rather than by renal disorders. Therefore, accurate assays of urine and other test samples for protein must be available for both laboratory and home use. The assays must permit the detection or measurement of the proteins of interest, such that a correct diagnosis can be made and correct medical treatment implemented, monitored and maintained. In addition, it would be advantageous if the protein assay method could be utilized in a dip-and-read format for the easy and economical, qualitative or quantitative determination of protein in urine or other test samples.

Furthermore, any method of assaying for protein in urine or other test samples must yield accurate, trustworthy and reproducible results by utilizing a method that provides a detectable or measurable color transition as a result of an interaction between the indicator reagent composition and the protein, and not as a result of a competing chemical or physical interaction, such as a pH change or preferential interaction with a test sample component other than protein. Moreover, it would be advantageous if the protein assay method is suitable for use in dry reagent strips for the rapid, economical and accurate determination of protein in urine and other test samples. Additionally, the method and test pad, comprising the carrier matrix and the indicator reagent composition, utilized in the assay for protein, and the new indicator reagent composition, should not adversely affect or interfere with the other test reagent pads that are present on multideterminant test pad strips.

Although a dry phase chemistry test strip utilizing a dye, such as tetrabromophenol blue or tetrachlorophenol-3,4,5,6-tetrabromosulfophthalein, has been used extensively for several years, no dry phase test strip has utilized a test pad comprising a carrier matrix, such as a filter paper, homogeneously impregnated with an indicator reagent composition including a hydrophobic polymeric compound as depicted above in general structural formula (I). The indicator reagent composition responds to urinary proteins and is essentially independent of urine specific gravity, thereby essentially eliminating the development of an interfering greenish-yellow color in the test pad by high SG samples including a negative amount of protein. Therefore, the assay exhibits an improved visual color resolution and an increased assay sensitivity, especially at lower protein concentration levels, to substantially reduce the number of false position assays. Surprisingly and unexpectedly, because of the essential elimination of the interferences related to urine specific gravity, the method of the present invention facilitates the dry phase test strip assay of urine and other test sample for albumin, especially at albumin levels of 0 mg/dL to about 30 mg/dL.

The prior art contains numerous references relating to the wet phase and the dry phase chemistry utilized in the pH indicator dye method of assaying urine for proteins. For example, Keston U.S. Pat. No. 3,485,587 discloses the basic dye binding technique used to assay for proteins at a constant pH. Keston teaches utilizing a single indicator dye, maintained at a constant pH slightly below the $pK_a$ (acid dissociation constant) of the dye and impregnated into a dry test paper, like filter paper, to determine the presence or concentration of albumin by monitoring the color transition of the dye. Free et al., in U.S. Pat. No. 3,095,277, also disclose a method of detecting the albumin content of liquid test samples by incorporating a suitable indicator composition into a bibulous carrier, like untreated filter paper. Similarly, Atkinson et al., in U.S. Pat. No. 3,438,737, disclose a test device comprising a test composition impregnated into an untreated bibulous matrix, such as filter paper, wood strips, synthetic plastic fibrous materials, nonwoven fabrics and woven fabrics for detecting protein in fluids.

Rittersdorf et al., in U.S. Pat. No. 4,013,416, disclose a test strip wherein an absorbent carrier is impregnated with an octahalosulfophthalein pH indicator dye, a buffer and a water-insoluble polypropylene glycol having a molecular weight of from about 500 to about 10,000 daltons. Rittersdorf et al. teach that the water-insoluble polypropylene glycol reduces the reactivity of the indicator dye with nitrogen containing compounds, such as metabolites of pharmaceuticals, thereby reducing the blank reaction in test strips. Rittersdorf et al. also teach only that water-insoluble propylene glycols are useful, e.g. polyethylene glycols are not useful. Rittersdorf et al. do not teach or suggest the usefulness of a polymer including a hydrocarbon, or essentially a hydrocarbon, backbone including pendant polyoxyalkylene units. In contrast, the indicator reagent composition of the present invention includes a hydrophobic polymeric compound having a hydrocarbon, or essentially hydrocarbon, backbone including 1 to about 8 alkylphenol units, like nonylphenol, linked by a methylene group or oxygen group, wherein the phenol moiety of each alkylphenol unit is ethoxylated and/or propoxylated to include about 2 and up to about 20 ethoxy and/or propoxy units in total.

The above-cited references do not teach or suggest, either alone or in combination, that an indicator reagent composition including a hydrophobic polymeric compound, as depicted above in general structural formula (I), can be used in a diagnostic device to achieve a more accurate determination of the amount of an analyte, like protein, and especially low amounts of an analyte, in a test sample. The references also do not teach or suggest, alone or in combination, that such an indicator reagent composition substantially reduces the number of false positive assays for albumin by essentially eliminating the effects of urine specific gravity in the assay for urinary proteins.

In contrast to the prior art, and in contrast to the presently available commercial test strips, the method of the present invention provides increased sensitivity in the detection and measurement of proteins in a liquid test sample, such as a biological fluid, like urine. Surprisingly and unexpectedly, by utilizing an indicator reagent composition, comprising an indicator dye, a buffer and a hydrophobic polymeric compound depicted by general structural formula (I), homogeneously impregnated into a carrier matrix, an assay of a test sample including a negative amount of protein (e.g., less than about 15 mg/dL) can be differentiated from an assay of a test sample including a trace amount of protein (e.g., about 15 to about 30 mg/dL) more accurately. Accordingly, the number of false positive assays is reduced substantially, and the number of unnecessary and costly confirmatory assays also is reduced. Hence, in accordance with the method of the present invention, new and unexpected results are achieved in the dry phase test strip assay of urine and other test samples for proteins by utilizing a test pad, comprising a carrier matrix having homogeneously incorporated therein an indicator reagent composition comprising an indicator dye, a buffer and a hydrophobic polymeric compound of general structural formula (I), that provides an accurate protein assay for samples including a negative to low trace amount of protein, and that is independent of the specific gravity of the test sample.

SUMMARY OF THE INVENTION

In brief, the present invention is directed to a new and improved method, test device and composition for determining the presence or concentration of a component in a test sample, especially negative to trace amounts of the component. The method includes using an indicator reagent composition capable of interacting with a test sample component to produce a detectable response. For home use, the indicator reagent composition produces a visually detectable response. For laboratory use, the indicator reagent composition produces a response that is detectable visually or by instrument. The method is suitable for a dry phase assay wherein the indicator reagent composition is incorporated into a carrier matrix of an analyte detection device. The carrier matrix of the analyte detection device comprises a bibulous porous material, such as filter paper, or a non-bibulous porous material, such as a permeable strip, layer or membrane of a polymeric material. An indicator reagent composition is homogeneously incorporated into the carrier matrix, and the carrier matrix then holds the indicator reagent composition homogeneously throughout the carrier matrix in a known concentration while maintaining carrier matrix penetrability for the liquid test sample.

More particularly, the present invention is directed to a method of assaying urine or other test samples for proteins, especially negative to trace quantities of proteins, by utilizing a new and improved indicator reagent composition. It has been demonstrated that employing an indicator reagent composition including an indicator dye, a buffer and a hydrophobic polymeric compound of general structural formula (I) affords sufficiently increased sensitivity and sufficient color resolution at low protein concentrations to permit the differentiation between a negative amount of protein, e.g., less than about 15 mg/dL, and a trace amount of protein, e.g., from about 15 to about 30 mg/dL, in a liquid test sample. The assay results are essentially independent of the specific gravity of the test sample. In accordance with an important feature of the present invention, the qualitative or quantitative determination of protein levels between 0 mg/dL and about 2000 mg/dL, and especially between 0 mg/dL and about 30 mg/dL, in urine and other test samples is accomplished.

By utilizing the indicator reagent composition of the present invention in clinical test methods, the qualitative or quantitative concentration of proteins, such as albumin, in urine or other test samples can be accurately determined, especially at negative to trace concentrations of protein, because the response of the indicator reagent composition is independent of the specific gravity of the test sample. Surprisingly and unexpectedly, the indicator reagent composition incorporated into the analyte detection device allows the differentiation between a negative protein concentration and between a trace protein concentration in urine and other test samples having a specific gravity in the range of 1.005 to about 1,030, thereby significantly reducing the number of false positive assays for protein in urine.

Therefore, one aspect of the present invention is to provide a new and improved test device, method and composition for determining the relative concentration of a chemical compound in a liquid. Another aspect of the present invention is to provide a simple, accurate and reproducible method of assaying urine or other test samples for proteins, especially at protein concentrations of 30 mg/dL and less.

Another aspect of the present invention is to provide a new and improved protein interactive test device for interaction with protein in a test fluid to produce a visible change, such as a change in color, of the test device, indicative of the protein concentration in the test fluid.

Another aspect of the present invention is to provide a method of assaying urine or other liquid test samples having sufficient sensitivity and sufficient visual color resolution to allow the differentiation between negative and trace protein concentrations.

Another important aspect of the present invention is to provide a method of assaying urine or other liquid test samples that is sensitive to protein concentrations of about 30 mg/dL and less, and that quantitatively discriminates between protein levels of 0 mg/dL to about 2000 mg/dL, and especially 0 mg/dL to about 30 mg/dL.

Another aspect of the present invention is to provide a method of assaying urine or other test liquids utilizing an indicator reagent composition that can interact with proteins and undergo a detectable and measurable color transition to establish the presence and concentration of protein in the test sample.

Another aspect of the present invention is to provide an indicator reagent composition that can interact with proteins and undergo a visually or instrumentally differentiable color transition to allow the quantitative determination of the concentration of protein in the urine or other liquid samples at levels between 0 mg/dL and about 2000 mg/dL, and especially between 0 mg/dL and about 30 mg/dL.

Another aspect of the present invention is to provide an indicator reagent composition that is capable of interacting with albumin and undergoing a color change, said indicator reagent composition comprising an (a) indicator dye; (b) a buffer; (c) a hydrophobic polymeric compound having the general structural formula (I):

wherein A is and PO is an oxypropylene unit, EO is an oxyethylene unit, y is a number in the range of 0 to about 20, z is a number in the range of 0 to about 20, the sum $y+z$ is a number in the range of about 2 to about 20, and $R_2$ and $R_3$ are selected, independently, from the group consisting of hydrogen, an alkyl group, an aralkyl group and an aryl group;

$R_1$ is either methylene or oxygen;

n is a number in the range of one to about 8; and

E is hydrogen or methylol when $R_1$ is methylene, or E is hydroxy when $R_1$ is oxygen; and (d) a suitable carrier comprising water.

Another important aspect of the present invention is to provide an indicator reagent composition capable of interacting with albumin and undergoing a color change and including a hydrophobic polymeric compound of general structural formula (I) wherein $R_2$ and $R_3$ are selected, independently, from the group consisting of hydrogen, an alkyl group including from one to about 22 carbon atoms, α-methylstyryl and phenyl; or wherein the moiety —A—$R_1$— of the hydrophobic polymeric compound of general structural formula (I) is selected from the group consisting of , and wherein $R_2'$ and $R_3'$ are, independently, hydrogen or an alkyl group including from one to about 22 carbon atoms.

Another important aspect of the present invention is to provide an indicator reagent composition for the assay of protein that includes a hydrophobic polymeric compound of general structural formula (I), wherein n is a number in the range of about 2 to about 5, and/or wherein the moiety —A—$R_1$— of the hydrophobic polymeric compound is wherein y' and z', independently, are numbers in the range of about 2 to about 8, and especially about 5 to about 6; the sum y'+z' is a number in the range of about 6 to about 16, and especially about 10 to about 12; and $R_2'$ is an alkyl group, linear or branched, including from about 6 to about 18, and especially from about 7 to about 12, carbon atoms. To achieve the full advantage of the present invention, $R_2'$ is an alkyl group including from about 8 to about 10 carbon atoms, like the $C_9H_{19}$ alkyl group.

Another aspect of the present invention is to provide a method of assaying for protein by incorporating an indicator reagent composition, including a hydrophobic polymeric compound of general structural formula (I), into a dry phase analyte detection device.

Still another aspect of the present invention is to provide a new and improved method of assaying for protein by utilizing an analyte test device including a carrier matrix having incorporated therein an indicator reagent composition capable of interacting with the protein content in a test sample, wherein the carrier matrix comprises a bibulous matrix, like filter paper, or a non-bibulous matrix, like a layer, film or membrane of permeable polymeric material.

BRIEF DESCRIPTION OF THE DRAWINGS

The above and other aspects and advantages and novel features of the present invention will become apparent from the following detailed description of the preferred embodiments of the invention illustrated in the accompanying figure demonstrating the increased sensitivity of test strips including an indicator reagent composition of the present invention to proteins, thereby permitting more accurate and differentiable analyte determinations.

DETAILED DESCRIPTION OF THE INVENTION

In accordance with the present invention, the qualitative or quantitative assay for proteins, such as albumin, and especially for negative to trace concentrations of proteins, in urine and other liquid test samples is accomplished by utilizing an indicator reagent composition including: (a) an indicator dye, (b) a buffer, (c) a hydrophobic polymeric compound depicted by general structural formula (I):

$$H\text{-}\!\!-\!\!(A\text{-}R_1\text{-})_n\!A\text{-}E, \qquad (I)$$

wherein A is and PO is an oxypropylene unit, EO is an oxyethylene unit, y is a number in the range of 0 to about 20, z is a number in the range of 0 to about 20, the sum y+z is a number in the range of about 2 to about 20, and $R_2$ and $R_3$ are selected, independently, from the group consisting of hydrogen, an alkyl group, an aralkyl group and an aryl group;

$R_1$ is either methylene or oxygen;

n is a number in the range of one to about 8; and

E is hydrogen or methylol when $R_1$ is methylene, or E is hydroxy when $R_1$ is oxygen, and (d) a suitable carrier comprising water. Preferably, $R_2$ and $R_3$ are, independently, hydrogen, a linear or branched alkyl group including from one to about 22 carbon atoms, α-methylstyryl or phenyl. In addition, the moiety —A—$R_1$— is preferably -continued wherein $R_2'$ and $R_3'$ are, independently, hydrogen or an alkyl group. To achieve the full advantage of the present invention, the hydrophobic polymeric compound of general structural formula (I) includes a moiety $-A-R_1-$ having the structure:

wherein $y'$ and $z'$ are, independently, numbers in the range of about 2 to about 8, and preferably about 5 to about 6; the sum $y'+z'$ is a number in the range of about 6 to about 16, and preferably about 10 to about 12; and $R_2'$ is an alkyl group, linear or branched, including from about 6 to about 18 carbon, and preferably from about 7 to about 12 carbon atoms; and/or n is a number in the range of about 2 to about 5. In an especially useful embodiment, $R_2'$ is a nonyl alkyl group ($C_9H_{19}$).

By employing an indicator reagent composition including a hydrophilic polymeric compound of general structural formula (I), the assay achieves a sufficient sensitivity to proteins and sufficient visual color resolution between protein levels to permit the differentiation between negative and trace concentration levels of proteins in liquid test samples. The improved sensitivity and color resolution to low protein levels afforded by the method of the present invention is especially useful in urine assays of test samples including from 0 to about 30 mg/dL protein because the nun%her of false positive assays for a trace amount of protein in urine is substantially reduced.

Present-day commercial assays do not effectively differentiate between protein concentrations in the range of 0 mg/dL to about 30 mg/dL, and especially between a test sample including less than about 15 mg/dL protein (a negative assay) and a test sample including from about 15 to about 30 mg/dL protein (a trace amount of protein). Differentiating between low protein concentration levels is important in the art because the range of 0 mg/dL to about 15 mg/dL is regarded as the normal urine protein level for a healthy individual. Therefore, urine protein levels of 0 mg/dL to about 15 mg/dL is a clinically negative result. A urine protein level greater than about 15 mg/dL, and up to about 30 mg/dL, is a clinically significant trace amount of protein that can signify a diseased state. Upon discovering a trace amount of urinary protein in a screening assay, the assay is confirmed by a different assay method.

Accordingly, to avoid performing unnecessary, and costly, confirmatory assays, it is important to provide an assay for urinary proteins that minimizes the number of false positive assays. It also should be noted that in regard to urine protein concentrations in the relatively high range, such as from about 30 mg/dL to about 2000 mg/dL, the method of the present invention still affords improved sensitivity and color resolution to urine protein concentration, however such clinical benefits are less critical in this concentration range since such high protein levels are definitely indicative of an abnormal physiological state that must be investigated further.

Presently, urine samples are screened for the presence of excess protein by contacting a dry phase test strip with the urine. The test strip includes a test pad having incorporated therein an indicator composition that undergoes a detectable change in response to the concentration of protein in the test sample. A common test pad incorporates an indicator composition including an octahalosulphophthalein indicator dye, a buffer and optional ingredients such as background dyes, surfactants and color stabilizers.

This common test strip detects only albumin. However, the test strip provides an excellent total urinary protein assay because albumin excretion correlates to total protein excretion. The coffeepot test strips are packaged with a reference chart having six standard color blocks determined from standardized albumin samples. The color chart corresponds to different protein concentrations and provides a rapid assay for urinary protein. The color chart provides six concentration ranges for urinary protein; the clinically normal range of negative (less than 15 mg/dL), the trace range (about 15 to about 30 mg/dL), and the pathological ranges of 30, 100, 300 and 2000 mg/dL. The color change produced over the entire range is yellow to yellowish-green to green to blue. For the negative range to trace range, the color change is from a greenish-yellow to a light green. Such a color change is difficult for an assayer to differentiate visually.

If the color change is interpreted as showing a trace amount of protein in the urine, a confirmatory assay of the urine is required. Accordingly, if the test strip provides a large number of false positive assays because of a poor color differentiation between a negative assay and a trace assay, a large number of time consuming and costly confirmatory assays would be performed needlessly. However, it has been difficult to provide a method and composition that affords a definite color differentiation between a negative assay and a trace assay, especially because a negative assay correlates to a normal amount of protein in the urine and because protein concentration is greater in urine having a high specific gravity.

For urine samples including a high protein concentration, e.g., about 100 mg/dL or greater, the color change for high specific gravity and low specific gravity urine samples are essentially identical. However, a specific gravity effect is observed in assaying urine samples including up to about 30 mg/dL of protein. For example, a high specific gravity urine sample including a clinically negative amount of protein provides a color change that closely matches the color change of a low specific gravity urine sample including a clinically significant trace amount of protein. Therefore, the assay of the negative high specific gravity urine can be interpreted, incorrectly, as including a clinically significant trace amount of protein. Then, the high specific gravity urine will be assayed by a confirmatory assay method, such as the SSA method, and the confirmatory assay will fail to find a clinically significant amount of protein in the urine. Therefore, the false positive screening test for albumin caused an unnecessary confirmatory assay to be performed.

The color displacement of an assay of a high specific gravity (SG) urine sample including a negative amount of protein toward the color exhibited by an assay of a sample including a trace amount of protein is referred to as a positive SG interference. This interference is the source of the false positive readings provided by present day test strips. It has been theorized that the positive interference attributed to a high SG urine sample is caused by at least two factors, i.e., the presence of quaternary ammonium compounds in the test sample and the buffering capacity of the test samples. Quaternary ammonium compounds include normal protein, peptides, amino acids and creatinine. All of these urinary components increase in concentration with increased specific gravity. Another factor that can cause positive SG interference is the buffering capacity of high SG urine samples, especially phosphate that shifts the pH upward by 0.1 unit.

In addition, a high SG urine sample shows a decreased reactivity to the indicator reagent composition at the positive protein levels of trace and above. Dose response plots for urinary protein assays consistently display a lower slope for high SG urine samples than for low SG urine samples. Hence, the differentiation between different color blocks becomes more difficult as SG increases, and is referred to as the negative SG interference. This decrease in color differentiation, especially in the trace to 30 mg/dL concentration range, provides a false negative assay. Therefore, the assayer is aware only of the false positive assays, since only positive results are confirmed. The assayer is unaware of false negative test strip readings. Therefore, it is necessary to eliminate the specific gravity of the urine test sample as a parameter in assaying urine samples in order to achieve an accurate protein assay in the range of 0 to about 30 mg/dL.

Furthermore, it will become apparent that in addition to assaying urine, the method and composition of the present invention also can be used to determine the presence or quantitative concentration of albumin in blood plasma or serum; and more generally, the albumin content of many other albumin-containing fluids as well. In accordance with another important feature of the present invention, the method and composition of the present invention is employed in dry phase, test pad assays to determine the presence or concentration of proteins, especially negative to trace concentrations of proteins, in urine or other liquid test samples.

Surprisingly and unexpectedly, an indicator reagent composition including a hydrophobic polymeric compound of general structural formula (I) demonstrated improved sensitivity and visual color resolution to negative to trace protein concentrations when used in a dye-binding technique to determine the presence or concentration of proteins in a test sample. The dye-binding technique using the hydrophobic polymeric compound of general structural formula (I) in the indicator reagent composition provides a more accurate, trustworthy and clinically significant assay especially for negative to trace concentrations of protein.

A test pad comprising an indicator reagent composition of the present invention incorporated into a suitable carrier matrix has demonstrated improved color resolution and increased sensitivity to low protein concentrations when used in a dye-binding technique to determine the presence or concentration of proteins in a test sample. The dye-binding technique using an indicator reagent composition of the present invention incorporated into a suitable carrier matrix provides a more accurate, trustworthy and clinically significant quantitative assay for protein in the range of 0 to about 30 mg/dL.

The indicator reagent compositions used in present day assay methods for protein interact with proteins and undergo a color transition due to the protein-error phenomena when maintained at the proper, constant pH. The protein-error phenomena is fully described in Free et al. U.S. Pat. No. 3,095,277; Atkinson et al. U.S. Pat. No. 3,438,737; and Keston U.S. Pat. No. 3,485,587, wherein the various dyes, the correct pH ranges, the buffers and the carrier matrices, such as bibulous substrates, like filter paper, required to observe the protein-error phenomena are disclosed. The three above-identified patents basically describe the present day, dry phase test strips employed to assay for total protein content in urine. These total protein test strips generally include an indicator reagent composition comprising an indicator dye that normally undergoes a color transition at a strongly acidic pH of 5 or below and a buffer to maintain the pH of the indicator dye slightly below the pH of color transition for the dye. A sufficient buffering of the indicator dye essentially assures that the dye changes color due to an interaction with protein rather than due to a pH change occurring upon contact with the test sample. The present day total protein test strips further include a carrier matrix, such as untreated or treated filter paper, for incorporation of the indicator reagent composition.

In accordance with an important feature of the present invention, the carrier matrix incorporates an indicator reagent composition of the present invention including a suitable indicator dye. A suitable indicator dye is capable of interacting with proteins, and is capable of undergoing a sufficient color transition due to the protein-error phenomena upon interaction with a protein to give a detectable or measurable response. However, in accordance with the present invention, it has been found that incorporating a suitable hydrophobic polymeric compound of general structural formula (I) into the indicator reagent composition substantially improves the color resolution and differentiation, both visually and instrumentally, of the color transition occurring upon interaction of the indicator dye with protein, especially when the test sample includes from 0 to about 30 mg/dL of protein. Therefore, the sensitivity of the protein assay, especially an low protein concentrations in the negative to trace range, is increased, and the number of false positive assays for urinary protein is substantially reduced.

The method of the present invention utilizes the "protein-error" phenomena previously discussed. However, the incorporation of a suitable hydrophobic polymeric compound of general structural formula (I) into the indicator reagent composition of the present invention improves the color resolution and differentiation of the color transition occurring because of the dye-protein interaction. As previously described, when a pH indicator dye interacts with a protein, the apparent $pK_a$ of the dye is altered and a color transition occurs producing the so-called "protein-error" phenomenon. A slight color transition, i.e., a background color, occurs even if the test sample includes a normal amount of protein, i.e., assays as negative. This slight color transition is sufficient to cause an incorrect interpretation of a negative assay as a trace assay. The development of a background color is attributed in most part to the reactivity of the indicator dye toward a positive SG interference. However, by employing the indicator reagent composition of the present invention, color development is essentially independent of test sample specific gravity. Consequently, color resolution and color differentiation upon interaction of the indicator dye with proteins is improved, assay sensitivity is increased, and the number of false positive assays is substantially reduced.

It has been demonstrated that the indicator reagent composition of the present invention provides an improved protein assay for an albumin-containing sample, and especially a sample containing 30 mg/dL or less protein, by essentially eliminating the positive SG interference. Thus, by essentially eliminating the positive SG interference, a negative assay for protein is maintained in the yellow region of the color space. The color resolution and color differentiation of the color transition resulting from assaying a test sample including 30 mg/dL or less albumin therefore are improved.

In general, any pH indicator dye can be utilized in the composition of the present invention, provided that the dye is capable of interacting with proteins and of undergoing a detectable and measurable color transition in response to the protein interaction. Such indicator dyes are well-known in the art and are utilized in indicator reagent compositions in methods to determine the presence or the concentration of protein in urine or other liquid test samples. In addition to the indicator dyes, it is known that the indicator reagent composition also may require a sufficient amount of a proper buffer, such that the indicator dye does not change color as a result of a pH shift, but changes color upon contact and interaction with proteins to accurately establish the presence or concentration of protein in the test sample. Further, it has been demonstrated that any of various known types of buffers can be used in the indicator reagent composition. For optimum results, it also has been found that the pH of the indicator reagent composition generally should be maintained at a pH value only slightly below the pH range wherein the indicator dye of the indicator reagent composition undergoes a color transition. A method of determining a suitable buffered pH value for the particular indicator dye of the indicator reagent composition and of determining the particular buffer that can be used in the indicator reagent composition is found in Keston, U.S. Pat. No. 3,485,587.

Furthermore, the indicator dye employed in the indicator reagent composition undergoes a sufficiently intense color transition such that relatively low concentrations of protein in the test sample produces a detectable and measurable color transition. Therefore, in order to achieve the full advantage of the present invention, the indicator dyes employed in the indicator reagent composition are selected such that the dye undergoes a sufficient color change either from a more intense color to a less intense color, or from a less intense color to a more intense color, such that the assayer, either visually or by instrument, can detect and measure the protein content of the test sample.

It has been found that the indicator dye used most advantageously in the composition and method of the present invention is an octahalosulfophthalein-type or an octahalophenolphthalein-type dye, such as tetrabromophenol blue, tetrachlorophenol blue, 3',3'',5',5''-tetraiodo-3,4,5,6-tetrabromophenolsulfophthalein and 3,3''-diiodo-5,5'',3,4,5,6-hexabromophenolsulfophthalein. These octahalosulfophthalein-type and octahalophenolphthalein-type dyes can undergo a sufficient color transition after binding to a protein to allow the visual or instrumental detection and measurement of the protein content of a test sample, including a negative to trace concentration of protein in the sample.

Depending upon several chemical and physical parameters, such as ability to interact with proteins, color of the test sample, intensity of the color transition and chemical compatibilities, a particular octahalosulfophthalein-type dye or octahalophenolphthalein-type dye is selected as the indicator dye of the indicator composition. The indicator dye generally is present in the indicator reagent composition in an amount of about 0.05 to about 0.6 millimoles per liter of the composition. However, the indicator dye can be present in a greater or lesser amount depending upon the intensity of the color transition of the particular indicator dye that is used. The exact octahalosulfophthalein-type dye or octahalophenolphthalein-type dye selected as the indicator dye of the indicator reagent composition can be determined by those skilled in the art of designing test kits in order to produce an assay for proteins having maximum visual color resolution and maximum sensitivity. The octahalosulfophthalein-type dye or octahalophenolphthalein-type dye utilized in the indicator reagent composition of the present invention can be prepared by methods well known to person in the art. Furthermore, several dye compounds that are useful in the method of the present invention are well known indicator dyes that are presently available commercially.

Further, it has been demonstrated that any of various known types of buffers can be used in the indicator reagent composition of the present invention. The function of the buffer is to maintain the composition at a substantially constant pH to produce the desired color change in the indicator reagent composition because of the presence of albumin and to essentially eliminate color changes due to a variation in the pH of the albumin-containing test sample. As a result, the amount of buffer used depends upon the nature of the test sample. The quantity of buffer usually falls between about 250 millimolar and 750 millimolar (millimoles per liter), although in particular cases the quantity of buffer can be above or below this range.

The nature of the particular buffer used will depend upon, and vary with, the indicator dye incorporated into the indicator reagent composition. However, it generally has been found that for optimum results, the pH of the indicator reagent composition should be maintained at a value only slightly below the pH range wherein the indicator dye undergoes a color transition. Useful buffers include, for example, but are not limited to, citric acid, maleic acid, tartaric acid, phthalic acid, sulfosalicylic acid, succinic acid, maleic acid, and malonic acid; their respective alkali metal and ammonium salts; and other suitable buffers are as well known in the art, or combinations thereof. A method of determining the proper pH for the particular indicator dye and the particular buffer used in the composition can be found in Keston, U.S. Pat. No. 3,485,587.

In addition to the indicator dye and the buffer, the indicator reagent composition includes a hydrophobic polymeric material having the general structural formula (I):

$$H \text{—} (A \text{—} R_1)_{\overline{n}} A \text{—} E, \qquad (I)$$

wherein A is and PO is an oxypropylene unit, EO is an oxyethylene unit, y is a number in the range of 0 to about 20, z is a number in the range of 0 to about 20, the sum y+z is a number in the range of about 2 to about 20, and $R_2$ and $R_3$ are selected, independently, from the group consisting of hydrogen, an alkyl group, an aralkyl group, and an aryl group;

$R_1$ is either methylene or oxygen;

n is a number in the range of one to about 8; and

E is hydrogen or methylol when $R_1$ is methylene, or E is hydroxy when $R_1$ is oxygen. The hydrophobic polymeric compound of general structural formula (I) has a molecular weight of about 800 to about 12,000, and preferably of about 1500 to about 8000. It has been found that a hydrophobic polymeric compound depicted by general structural formula (I) reduces the development of a background color; reduces positive interferences attributed to urinary components other than proteins; and substantially reduces the positive interferences attributed to high specific gravity samples that, in turn, lead to false positive assays in dry phase test strip assays.

As will be discussed more fully hereinafter, it has been shown that about 1% to about 8%, and preferably about 2% to about 6%, by weight of a hydrophobic polymeric compound of general structural formula (I), per milliliter of indicator reagent composition, provides a test pad that remains a light yellow color after contact with a high SG (specific gravity) or a low SG urine sample that is free of albumin. In contrast, a test pad incorporating a reagent composition lacking the hydrophobic polymeric compound of general structural formula (I) changes to a greenish-yellow color after contact with a high SG urine sample free of albumin. This color transition from yellow to greenish-yellow can be interpreted, incorrectly, as a clinically significant trace amount of albumin and therefore provide a false positive assay. The test sample then would be subjected to an unnecessary and costly confirmatory assay for albumin.

With regard to a hydrophobic polymeric compound of general structural formula (I), preferably, $R_2$ and $R_3$ are, independently, hydrogen, a linear or branched alkyl group including from one to about 22 carbon atoms, α-methylstyryl or phenyl. In addition, the moiety —A—$R_1$—preferably is wherein $R_2'$ and $R_3'$ are, independently, hydrogen or an alkyl group including one to about 22 carbon atoms. To achieve the full advantage of the present invention, the hydrophobic polymeric compound of general structural formula (I) includes the number n in the range of about 2 to about 5 and/or includes a moiety —A—$R_1$—having the structure:

wherein y' and z' are, independently, numbers in the range of about 2 to about 8, and preferably from about 5 to about 6; the sum y'+z' is a number in the range of about 6 to about 16, and preferably about 10 to about 12; and $R_2'$ is an alkyl group, linear or branched, including from about 6 to about 18, and preferably from about 7 to about 12, carbon atoms.

A particularly useful hydrophobic polymeric compound of general structural formula (I) is depicted in structural formula (II), referred to hereinafter as polymer II. Polymer II has a molecular weight of about 2200.

$$\text{(II)}$$

In addition to the essential ingredients, other optional ingredients that do not materially alter the nature or the function of the essential ingredients, and that do not interfere with the assay for proteins, also can be included in the indicator reagent composition. For example, the indicator reagent composition optionally can include a compound to improve test sample wetting of the test pad of the test device. The optional wetting compound usually is a nonionic surfactant. The octoxynols, nonoxynols and ethoxylated fatty alcohols are nonlimiting examples of nonionic surfactants useful as the wetting compound in the indicator reagent composition of the present invention. The wetting compound is included in the indicator reagent composition in a concentration of 0 nM to about 200 mM, and preferably in a concentration of from about 50 nM to about 200 mM.

In addition, to improve the color resolution and differentiation of the color transition in a chromogenic assay for proteins, inert background dyes can be included in the indicator reagent composition. Suitable background dyes include, but are not limited to, ethyl orange (4-(4-diethylaminophenylazo)benzenesulfonic acid); Orange G (4-(2-hydroxy-(7,9 sodium disulfonate)-1-naphthylazo)benzene); disperse orange 11, 13, or 25; calcomine orange; methyl orange; and orange II (4-(2-hydroxy-1-naphthylazo)benzenesulfonic acid), or combinations thereof. A background dye is included in the indicator reagent composition of the present invention in a concentration of 0 mM to about 2 mM, and preferably about 0.1 mM to about 1 mM.

The carrier vehicle for the ingredients included in the indicator reagent composition includes water. However, because of the limited water solubility of particular ingredients included in the indicator reagent composition, organic solvents such as methanol, ethanol, isopropyl alcohol, ethylene glycol, propylene glycol, acetone, dimethylformamide, dimethylsulfoxide, acetonitrile, ethyl acetate and similar solvents can be used to solubilize the water-insoluble ingredients. The selection of a suitable organic solvent or combination of organic solvents to include in the carrier vehicle of the indicator reagent composition is within the capability of those skilled in the art of designing diagnostic test strips.

Furthermore, it should be understood that the indicator reagent composition can be composed of two distinct solutions, one aqueous-based and one organic solvent-based, to solubilize the water soluble and the water insoluble components respectively. In such a case, the amount of each ingredient present in the composition is determined using the total volume of the two distinct solutions. As will be demonstrated more fully hereinafter, the carrier matrix then can be subjected to two treatments. Accordingly, a first solution, either the aqueous or the organic solvent-based solution, is incorporated into the carrier matrix, then the second solution is incorporated into the carrier matrix in order to homogeneously incorporate each essential ingredient of the indicator reagent composition into the carrier matrix.

Upon contact with the urine or other test sample, a color transition of the indicator reagent composition demonstrates the presence of protein. Furthermore, the intensity and degree of the color transition can be used to determine the quantitative concentration of protein in the test sample by comparing or correlating the color produced by the test sample to colors produced by solutions having a known concentration of protein. In accordance with an important feature of the present invention, it has been demonstrated that the indicator reagent composition provides a sufficiently resolved and differentiated color transition such that the amount of protein, including negative to trace amounts of protein, in the test sample can be measured and accurately determined without the use of color-measuring instruments, such as spectrophotometers or colorimeters. However, if desired, such color-measuring instruments can be used to measure the difference in color degree and intensity between the test sample and a solution of known albumin concentration. In addition, it has been demonstrated that the assay is essentially independent of urine specific gravity, thereby substantially reducing the number of false positive assays.

Accordingly, an assay for protein that utilizes an indicator reagent composition of the present invention including a hydrophobic polymeric compound of general structural formula (I) improves the accuracy and reliability of the assay and also increases physician confidence in the assay. Additionally, because of the number of urine assays for protein being performed at home by the untrained patient, as opposed to trained physicians or technicians in the laboratory, it is imperative to provide accurate and reliable quantitative assay methods for negative to trace protein content in a urine sample to reduce the number of false positive assays resulting from urine specific gravity.

In general, assays for protein are conducted at an acidic pH using an indicator dye undergoing a color transition at an acidic pH because the indicator dye can interact more strongly with the protein at low, acidic pH values. The increased interaction between the indicator dye and the protein at low pH values occurs because of a strong attraction between the positively-charged cationic protein molecule and the negatively-charged anionic indicator dye molecule, and, additionally, because the acidic conditions serve to partially denature proteins and therefore increase the ability of the protein to interact with the indicator dye. Therefore, the indicator reagent composition of the present invention generally is adjusted to and maintained at an acidic pH. Generally, the pH of the system is adjusted to and maintained at between about 2 and about 4; and to achieve the full advantage of the present invention the pH is adjusted to and maintained at between about 3 and 4.

To demonstrate the new and unexpected results achieved by the method and composition of the present invention, an indicator reagent composition, including a hydrophobic polymeric compound of general structural formula (I), was prepared, then used in a dry phase test strip assay for the total protein content of a test sample. The indicator dye, tetrabromophenol blue (TBPB), interacts with proteins and undergo a color transition at a pH of about 3.5. The TBPB is yellow in color in the absence of proteins and changes color ranging from yellowish-green, to green to blue in the presence of increasing amounts of proteins. As a result, an indicator reagent composition including the appropriate amount of TBPB, adjusted to and maintained at a pH of 3.5 with a suitable buffer, produced the color transitions summarized in TABLE I upon contact with standardized protein solutions.

TABLE I

COLOR TRANSITION OF TBPB-CONTAINING INDICATOR REAGENT COMPOSITION UPON INTERACTION WITH STANDARDIZED PROTEIN SOLUTIONS (pH = 3.5)

| Concentration of Standardized Protein Solution (mg/dL) | Observed Color |
|---|---|
| 0–15 (negative) | yellow |
| 15–30 (trace) | yellowish green |
| 30 | light green |
| 100 | medium green |
| 300 | blue green |
| 2000 | dark blue green |

The dry phase, test pad assay for albumin utilizing an indicator reagent composition of the present invention is performed in accordance with methods well known in the art. In general, the albumin assay is performed by contacting an analyte detection device with the urine or other test sample. The analyte detection device comprises a test pad incorporating the indicator reagent composition. The analyte detection device can be dipped into the urine or serum sample, or the urine or serum sample can be applied to the analyte detection device dropwise. A change in color of the test pad of the device demonstrates the presence of albumin, and, if so designed, the intensity and depth of the color change can be compared to a color chart to afford a quantitative measurement of the concentration of albumin in the test sample.

Typically, the analyte detection device is a test strip impregnated with a reagent composition, designed either as a single pad test strip (to assay for a single analyte) or as a multiple pad test strip (to assay for several analytes simultaneously). For either type of reagent impregnated test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents. The carrier matrix also is porous or absorbent relative to the liquid test sample.

The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Non-absorptive substances are not suitable for use as the carrier matrix of the present invention. However, a hard, porous plastic is useful as the carrier matrix as long as the plastic is sufficiently porous to allow the test sample to permeate through the plastic and contact the indicator reagent composition. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate or polystyrene, and the carrier matrix is most advantageously constructed from bibulous filter paper or nonbibulous permeable polymeric films.

To achieve the full advantage of the present invention, the indicator reagent composition is homogeneously incorporated into a suitable carrier matrix and utilized in a dry phase test strip for the assay or protein in a test sample. The method of the present invention affords an economical, accurate and reliable assay for the total concentration of protein in test samples that can be performed at home or in the laboratory. In addition, the method of the present invention is essentially independent of test sample specific gravity, and allows detection of, and differentiation between, negative and trace protein concentrations in a test sample thereby making the assay more useful clinically.

In accordance with the method of the present invention, to perform a dry phase, test strip assay for protein, an aqueous solution, including from about 250 mM (millimolar, or millimoles per liter) to about 750 mM total concentration of a buffer, such as potassium citrate, adjusted to a pH of about 3.5, first is prepared. A bibulous matrix, such as filter paper, like WHATMAN CCP500 filter paper, available commercially from Whatman Ltd., Maidstone, Kent, U.K., then is saturated with the aqueous solution containing the buffer either by spreading, by immersing or by spraying the aqueous solution onto sheets or precut strips of the filter paper. The aqueous solvent is removed from the filter paper by oven drying in an air oven at about 50° C. for about 20 minutes.

Then, a tetrahydrofuran (THF) or ethanol solution, including about 0.05 to about 0.6 mM of an indicator dye, like about 0.3 mM of TBPB, and from about 1% to about 8%, by weight volume, of a hydrophobic polymeric compound of general structural formula (I), like 5% (w/v) of polymer II, is prepared. The strip of dried filter paper incorporating the citrate buffer then is saturated with the THF or ethanol solution including the indicator dye and the polymer II. After removing the THF or ethanol solvent by oven drying at about 50° C. for about 15 to about 30 minutes, the reagent impregnated filter paper strip is cut to an appropriate size, such as a pad having dimensions from about 0.25 cm by about 0.5 cm to about 0.5 cm by about 1.0 cm. The reagent impregnated filter paper pad then is secured to a plastic handle with double sided adhesive to provide a test strip.

The test strip then was dipped into a fresh, uncentrifuged urine sample for a sufficient time to saturate the test pad with the sample. The test strip should not be immersed in the urine sample for longer than about 3 to 5 seconds in order to avoid extraction of the buffer from the filter paper by the urine sample. After removing the test strip from the urine sample and waiting a predetermined time, such as from about 1 minute to about 2 minutes, the test strip is examined, either visually or by instrument, for a response. The color transition, if any, of the test pad reveals the presence and/or concentration of protein in the urine sample.

It is well within the experimental techniques of those skilled in the art of preparing test devices to determine the proper balance between size of reagent pad, the strength of the indicator reagent composition, the amount of test sample, and the method of introducing the test sample to the test strip, such as by piperting rather than dipping, in order to design a quantitative assay for protein utilizing the method and composition the present invention.

In many cases simple visual observation of the test strip provides the desired information. If more accurate information is required, a color chart bearing color spots corresponding to various know protein concentrations, can be prepared for the particular indicator reagent composition incorporated into the test strip. The resulting color of the test strip after contact with the urine sample then can be compared with the color spots on the chart to determine the protein concentration of the test sample.

If a still more accurate determination is required, a spectrophotometer or colorimeter can be used to more precisely determine the degree of color transition. In addition, the dry phase test strip assay can be made quantitative by employing spectrophotometric or colorimetric techniques, as opposed to visual techniques, in order to more reliably and more accurately measure the degree of color transition, and therefore more accurately measure the concentration of protein in the test sample, especially at lower protein concentrations, such from 0 mg/dL to about 30 mg/dL.

As will be discussed more fully hereinafter, the ability to detect and differentiate between negative and trace concentrations of protein in a test sample by employing an indicator reagent composition of the present invention surprisingly and unexpectedly provides an improved method of assaying for the total protein content of liquid test samples. For example, according to present day methods, differentiation between an assay indicating a clinically significant trace amount of protein (e.g., about 15 to about 30 mg/dL protein) and a negative assay (e.g., about 15 mg/dL protein or less) is difficult, thereby resulting in a large number of false positive assays.

A major cause of false positive assays is the dependence of the protein assay on test sample specific gravity. Accordingly, until the method of the present invention, no dry phase test strip technique either was essentially independent of test sample specific gravity or was available to consistently differentiate between the negative and trace concentrations of protein often found in urine. Therefore, in accordance with an important feature of the present invention, it has been demonstrated that by incorporating an indicator reagent composition of the present invention into a suitable carrier matrix, the presence of a negative or a trace concentration of protein in a urine sample can be determined, and differentiated from one another, by using a dry phase test strip that is essentially independent of the specific gravity of urine sample.

To show the new and unexpected results achieved by using the indicator reagent composition of the present invention, test strips incorporating an indicator reagent composition of the present invention were prepared, and then were compared to prior art test strips in assays of standardized urine samples including albumin in the range of 0 mg/dL to about 30 mg/dL. First, two sets of dry phase test strips were prepared by the two immersion procedure described above. All the test strips utilized WHATMAN CCP500 filter paper as the carrier matrix. All the test strips were immersed into a 0.50M potassium citrate solution buffered at pH 3.5, then dried. Then, a portion of the test strips, Test Strips A, had incorporated therein a 0.30 mM solution of TBPB in THF. Test Strips A are prior art test strips. The remaining test strips incorporating the citrate buffer had incorporated therein a THF solution that was 0.30 mM in TBPB and included 5% (w/v) polymer II. These test strips, Test Strips B, incorporated an indicator reagent composition of the present invention.

Test Strips A were compared to Test Strips B for an ability to detect 0 mg/dL to 30 mg/dL albumin in a urine sample. In particular, a urine pool, having a low SG of about 1,007 and shown by immunoassay to be free of albumin, was spiked to various clinically significant albumin levels with human serum albumin. The spiked urine samples included either 0, 10, 15, 20 or 30 mg/dL of albumin. These standardized urine samples then were used to compare Test Strips A to Test Strips B for an ability to detect urinary protein and to differentiate between urinary protein assays in the range of 0 mg/dL to about 30 mg/dL protein.

Figure 1:
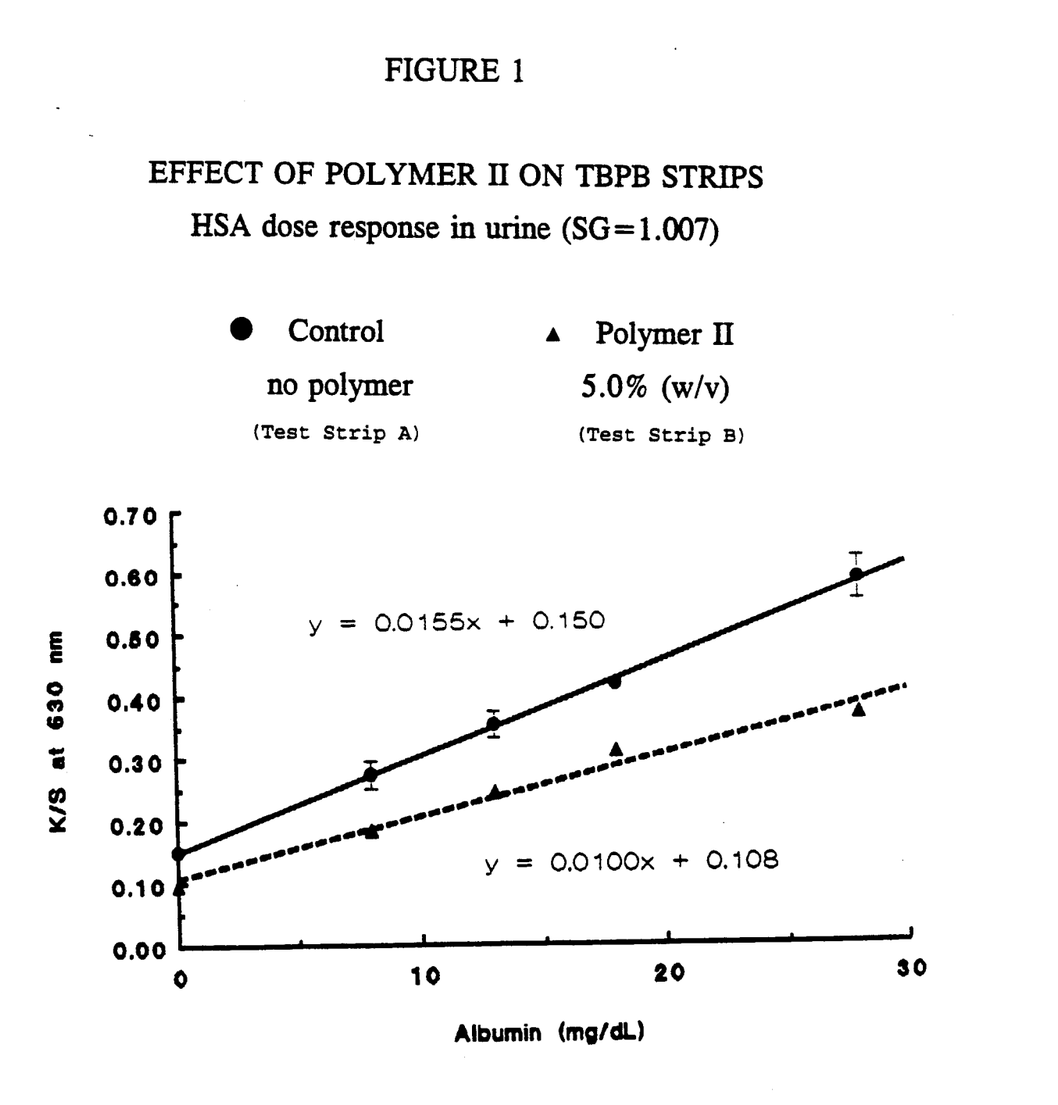
FIG. 1 is a dose response plot for albumin concentration (in mg/dL) vs. the Kubelka-Munk function (K/S) for reflectance at 630 nm (nanometers) comparing test strips incorporating an indicator reagent composition including a hydrophobic polymeric compound of general structural formula (I) to test strips incorporating an indicator reagent composition absent a hydrophilic polymeric compound.

Test Strips A and Test Strips B each were immersed into the standardized urine samples, then examined for a response to the protein content of the test sample. FIG. 1 illustrates the dose responses to albumin for Test Strips A and Test Strips B. In particular, FIG. 1 includes two dose response plots for albumin concentration (mg/dL) rs. K/S at 630 nm (nanometers). Individual assay results were determined by taking a reflectance measurement with a reflectance photometer at a suitable time and wavelength for that particular analyte determination. The reflectance, as taken from the reflectance scale of zero to one, was incorporated into the Kubelka-Munk function:

$$K/S = (1-R)^2/2R,$$

wherein K is the absorption coefficient, S is the scattering coefficient and R is reflectance. In FIG. 1, the K/S values were plotted against the concentration of albumin in the test sample. Generally, it can be stated that as reflectance decreases, the K/S value increases.

Therefore, the two dose response plots of FIG. 1 show the effects of increased albumin concentration on the K/S values and the effect of including a hydrophobic polymeric compound of general structural formula (I) in the indicator reagent composition. The reflectance was measured at a wavelength of 630 nm (nanometers), then the K/S values were calculated. The K/S values are the average K/S values for three replicate determinations.

From FIG. 1, it is observed that as the albumin concentration increases the K/S value also increases. Therefore, the reflectance has decreased, indicating a greater color transition in the test pad. It also is observed from the dose response plots of FIG. 1 that including a hydrophobic polymeric compound of general structural formula (I), e.g., polymer II, in the indicator reagent composition lowers both the intercept and the slope of the human serum albumin (HSA) dose response plot, as illustrated by the dashed line of FIG. 1, compared to an indicator reagent composition lacking the polymer, as illustrated by the solid line of FIG. 1.

It should be noted that the lowering of the intercept from about 0.150 to about 0.108 by a composition of the present invention is an important and unexpected result. FIG. 1 shows that the prior art reagent composition incorporated into Test Strips A and the indicator reagent composition of the present invention incorporated into Test Strips B each have a sufficient sensitivity to the amount of albumin in the standardized urine sample. But the lower intercept provided by the indicator reagent composition of the present invention incorporated into Test Strips B maintains the definite yellow color of the test pad after a Test Strip B contacts a test sample including 0 mg/dL albumin, whereas a Test Strip A becomes a yellowish-green color after contact with a test sample including 0 mg/dL albumin. For comparative purposes, a K/S value in the range of about 0.2 to about 0.4 corresponds to a trace amount of protein in the urine sample. A test pad having a K/S value of about 0.2 is visualized as a light greenish-yellow color. A trace amount of protein begins at a protein concentration of about 15 mg/dL.

Accordingly, the yellowish-green color of Test Strip A can be interpreted incorrectly as including a trace concentration (about 15 mg/dL) of albumin when the test solution only contains approximately 5 mg/dL albumin. However, Test Strip B will correctly only turn greenish-yellow at a trace concentration (about 15 mg/dL) of albumin in a test sample. Therefore, an indicator reagent composition of the present invention, including a hydrophobic polymeric compound of general structural formula (I), helps maintain the color of the test pad in the negative assay range, thereby substantially reducing the number of false positive assays for a trace amount of albumin. Consequently, substantially fewer unnecessary confirmatory assays for trace albumin are conducted.

The Test Strips A and Test Strips B also were compared in the assay of a high specific gravity (SG=1.023) urine sample that was shown by an immunoassay to be free of albumin. The assay results for both the low SG urine sample and the high SG urine sample including no albumin (i.e., a negative sample), and used to compare a Test Strip A to a Test Strip B, are summarized below. Both the high SG urine sample and the low SG urine sample included 0 mg/dL albumin.

| K/S at 630 nm (25 seconds), 0 mg/dL Albumin | | |
|---|---|---|
| Test Strip | Low SG Sample | High SG Sample |
| A | 0.151 ± 0.010 | 0.199 ± 0.013 |
| B | 0.097 ± 0.002 | 0.102 ± 0.003 |

From the summarized data, it is observed that a high SG urine sample, including a negative amount of albumin (0 mg/dL), exhibits a value of 0.199 when a prior art indicator reagent composition is incorporated into a test pad (Test Strip A). In contrast, a low SG urine sample including a negative amount of albumin and assayed by a prior art indicator reagent composition exhibits a value of 0.151. As discussed above, the 0.151 value of the low SG urine sample appears as a greenish-yellow color for the blank reaction that can be interpreted incorrectly as a trace amount of protein. Accordingly, the value of 0.199 exhibited by the high SG urine sample provides a greenish-yellow color for the blank reaction that is displaced even further into the green color region, and thereby is more easily interpreted incorrectly as a clinically significant positive assay for a trace amount of protein.

Therefore, the prior art compositions used in assays for protein provided an unacceptably large number of false positive assays because the color change of the test strip is directly related to the specific gravity of test sample. A high SG urine sample showed a significant increase in test strip reactivity over a low SG urine sample, and accordingly, a greater number of false positive assays. In contrast, an indicator reagent composition of the present invention, including a hydrophobic polymeric compound of general structural formula (I), essentially eliminates specific gravity as a parameter in the dry phase test strip assay for proteins.

As previously discussed, a test strip incorporating an indicator reagent composition of the present invention (Test Strips B) lowers the K/S value to 0.097 for a low SG urine sample including 0 mg/dL albumin, compared to a K/S value of 0.151 for test strips incorporating a prior art composition (Test Strips A). As explained, this reduction in the reactivity provides a test pad exhibiting a yellow color in the assay of low SG urine samples including a negative amount of albumin. Surprisingly, a high SG urine sample including a negative amount of albumin (0 mg/dL) exhibits a K/S value of 0.102 when assayed by a Test Strip B incorporating a composition of the present invention. This reactivity also provides a test pad exhibiting a yellow color that is easily interpreted as a negative assay for albumin. Therefore, it has been shown that test sample specific gravity essentially does not effect the color change exhibited by a test pad incorporating an indicator reagent composition of the present invention. Consequently, fewer false positive assays for protein result.

The summarized data also shows that a high SG urine sample assayed with a test strip including a prior art composition exhibits a K/S value of 0.199 and a definite greenish-yellow colored test pad, whereas a high SG urine sample assayed with a test strip including the present composition exhibits a K/S value of 0.102 and a yellow colored test pad. Therefore, it has been shown that the present indicator reagent composition reduces the reactivity of a test strip in the presence of a high SG urine sample, and substantially reduces the occurrence of false positive assays due to interferents present in high SG urine samples.

As a result, it has been demonstrated that using the present indicator reagent composition to detect the presence and concentration of proteins in a test sample, surprisingly and unexpectedly allows the detection of, and differentiation between, a negative and a trace amount of protein in a test sample. In addition, the assay is essentially independent of, and is not adversely influenced by, the specific gravity of the test sample. Such unexpected improvements provide an important and useful advantage over prior art indicator reagent compositions that lack a hydrophobic polymeric compound of general structural formula (I), and that are used to assay for the protein content of test samples. As illustrated in FIG. 1 and in the data summarized above, the prior methods and compositions suffer from both a severe specific gravity interference and an inability to effectively differentiate between a negative albumin concentration of about 15 mg/dL or less and a clinically significant trace albumin concentration of about 15 to about 30 mg/dL. However, in contrast, an assayer, using a test device incorporating an indicator composition of the present invention to assay for albumin in a test sample, can reliably assay test samples for total protein concentration, including negative and trace amounts of protein, without generating an unacceptably large number of false positive assays.

It should be understood that those skilled in the art of designing test kits are able to design an optimal test strip incorporating a sufficient amount of a particularly effective indicator reagent composition, comprising an indicator dye, a buffer and a hydrophobic polymeric compound of general structural formula (I), to permit the detection of, and the differentiation between, negative and trace amounts of albumin in a test sample because assays utilizing the method and composition of the present invention showed a visually detectable color difference and were independent of the specific gravity of the test sample. The method and composition of the present invention allow the assayer to differentiate between a test sample containing about 15 mg/dL or less of albumin and a test sample containing about 15 to about 30 mg/dL of albumin, thereby substantially reducing the number of false positive assays.

Overall, it has been shown that an indicator reagent composition of the present invention incorporated into a suitable carrier matrix, such as filter paper, improves the color resolution of assays between test samples having different protein concentrations and eliminates false positive results for the total protein content of a liquid test sample, especially at low protein levels of about 30 mg/dL or less. In addition, the present composition is not subject to specific gravity interferences. The method and composition of the present invention also allow visual differentiation of color transitions resulting from contact of the carrier matrix impregnated with the present indicator reagent composition with a test sample containing protein levels of between 0 mg/dL and 30 mg/dL, thereby providing accurate and trustworthy assays of test samples containing negative to trace amounts of protein, without generating an unacceptably high number of false positive assays.

Therefore, in accordance with an important feature of the present invention, more accurate and reliable assays for total protein content, and especially for negative or trace total protein content, in urine and other liquid test samples can be performed by utilizing an indicator reagent composition including a hydrophobic polymeric compound of general structural formula (I). The present indicator reagent composition improves the color resolution of the test strips between test samples having different protein concentrations, and therefore improves assay sensitivity, especially at negative to trace albumin levels of approximately 30 mg/dL and below.

Obviously, many modifications and variations of the invention as hereinbefore set forth can be made without departing from the spirit and scope thereof and therefore only such limitations should be imposed as are indicated by the appended claims.

What is claimed is:

1. An indicator reagent composition capable of exhibiting a sufficient color transition upon contacting a protein-containing test sample to demonstrate the presence or concentration of protein in the test sample consisting essentially of:
  (a) an indicator dye capable of interacting with a protein and exhibiting a color transition upon such interaction, said indicator dye being present in an amount of about 0.05 to about 0.6 millimoles per liter of the composition and wherein the indicator dye is selected from the group consisting of 3',3'',5,5''-tetraiodo-3,4,5,6-tetrabromophenolsulfophthalein, 3,3''-diiodo-5,5'',3,4,5,6-hexabromophenolsulfophthalein, and combinations thereof;
  (b) a buffer present in an amount of about 250 to about 750 millimoles per liter of the composition wherein the buffer is selected from the group consisting of citric acid, maleic acid, tartaric acid, phthalic acid, sulfosalicyclic acid, succinic acid, malonic acid, their respective alkali metal and ammonium salts and combinations thereof;
  (c) a hydrophobic polymeric compound present in an amount of about 1% to about 8% by weight per milliliter of the composition having the general structural formula:

$$H-[-A-R_1-]_n-A-E,$$

wherein A is and PO is an oxypropylene unit, EO is an oxyethylene unit, y is a number in the range of 0 to about 20, z is a number in the range of 0 to about 20, the sum of y+z is a number in the range of about 2 to about 20, and $R_2$ and $R_3$ are selected, independently, from the group consisting of hydrogen, alkyl group, an aralkyl group, and an aryl group;
  $R_1$ is methylene or oxygen;
  n is a number in the range of 1 to about 8; and
  E is hydrogen or methylol when $R_1$ is methylene, or E is hydroxy when $R_1$ is oxygen; and
  (d) a carrier vehicle for said composition.

2. The composition of claim 1 wherein the buffer buffers the composition at a pH of 2 to 4.

3. The composition of claim 1 wherein the hydrophobic polymeric compound is present in the amount of about 2% to about 6%, by weight, per milliliter of the composition.

4. The composition of claim 1 wherein the hydrophobic polymeric compound has a molecular weight in the range of about 800 to about 12,000.

5. The composition of claim 1 wherein the substituents $R_2$ and $R_3$ of the hydrophobic polymeric compound are selected, independently, from the group consisting of hydrogen, an alkyl group including from one to about 22 carbon atoms, α-methylstyryl, and phenyl.

6. The composition of claim 1 wherein the moiety —A—$R_1$— of the hydrophobic polymeric compound is , or wherein $R_2'$ and $R_3'$ are, independently, hydrogen or an alkyl group including one to about 22 carbon atoms.

7. The composition of claim 1 wherein n is a number in the range of about 2 to about 5.

8. The composition of claim 1 wherein the moiety $—A—R_1—$ of the hydrophobic polymeric compound is wherein PO is an oxypropylene unit, EO is an oxyethylene unit, y' and z' are, independently, numbers in the range of about 2 to about 8, the sum $y'+z'$ is a number in the range of about 6 to about 16; and $R_2'$ is an alkyl group including from about 6 to about 18 carbon atoms.

9. The composition of claim 8 wherein y' and z' are, independently, numbers in the range of about 5 to about 6; the sum $y'+z'$ is a number in the range of about 10 to about 12; and $R_2'$ is an alkyl group including from about 7 to about 12 carbon atoms.

10. The composition of claim 1 having a buffered pH in the range of about 2 to about 4.

11. The method of contacting a test sample with an indicator reagent composition to determine the presence of concentration of protein in the test sample, said method being essentially free of interferences attributed to specific gravity, said method comprising the steps of:
(i) contacting the test sample with an indicator reagent composition consisting essentially of:
(a) an indicator dye capable of interacting with a protein and exhibiting a color transition upon such interaction, said indicator dye being present in an amount of about 0.05 to about 0.6 millimoles per liter of the composition and wherein the indicator dye is selected from the group consisting of 3',3'',5,5''-tetraiodo-3,4,5,6-tetrabromophenolsulfophthalein, 3,3''-diiodo-5,5'',3,4,5,6-hexabromophenolsulfophthalein, and combinations thereof;
(b) a buffer present in an amount of about 250 to about 750 millimoles per liter of the composition wherein the buffer is selected from the group consisting of citric acid, maleic acid, tartaric acid, phthalic acid, sulfosalicylic acid, succinic acid, malonic acid, their respective alkali metal and ammonium salts and combinations thereof;
(c) a hydrophobic polymeric compound present in an amount of about 1% to about 8% by weight per milliliter of the composition having the general structural formula:

$$H—[—A—R_1—]_n—A—E,$$

wherein A is and PO is an oxypropylene unit, EO is an oxyethylene unit, y is a number in the range of 0 to about 20, z is a number in the range of 0 to about 20, the sum of $y+z$ is a number in the range of about 2 to about 20, and $R_2$ and $R_3$ are selected, independently, from the group consisting of hydrogen, alkyl group, an aralkyl group, and an aryl group;
$R_1$ is methylene or oxygen;
n is a number in the range of 1 to about 8; and
E is hydrogen or methylol when $R_1$ is methylene, or E is hydroxy when $R_1$ is oxygen; and
(d) a carrier vehicle for said composition; and
(ii) determining the presence or concentration of protein in the test sample from a resulting intensity or degree of the color transition of the indicator reagent composition.

12. The method of claim 11 wherein the intensity and degree of the color transition is determined visually or by instrument.

13. The method of claim 11 wherein the presence or concentration of protein is determined by a dry phase assay.

14. The method of claim 11 wherein the test sample is a biological sample.

15. The method of claim 14 wherein the biological sample is urine, blood plasma or blood serum.

16. The method of claim 15 wherein the urine has a specific gravity of about 1.005 to about 1.030.

17. The method of claim 11 wherein the test sample includes from 0 mg/dL protein to about 30 mg/dL protein.

18. The method of claim 11 wherein the buffer buffers the indicator reagent composition at a pH of 2 to 4.

19. The method of claim 11 wherein the number n of the hydrophobic polymeric compound is in the range of about 2 to about 5.

20. The method of claim 11 wherein the moiety —A—R$_1$— of the hydrophobic polymeric compound is

,

, or

, wherein R$_2'$ and R$_3'$ are, independently, hydrogen or an alkyl group including one to about 22 carbon atoms.

21. The method of claim 20 wherein n is a number in the range of about 2 to about 5.

22. The method of claim 11 wherein the moiety —A—R$_1$— of the hydrophobic polymeric compound is

, wherein PO is an oxypropylene unit, EO is an oxyethylene unit, y' and z' are, independently, numbers in the range of about 2 to about 8, the sum y'+z' is a number in the range of about 6 to about 16; and R$_2'$ is an alkyl group including from about 6 to about 18 carbon atoms.

23. The method of claim 22 wherein y' and z' are, independently, numbers in the range of about 5 to about 6; the sum y'+z' is a number in the range of about 10 to about 12; and R$_2'$ is an alkyl group including from about 7 to about 12 carbon atoms.

24. The method of claim 11 wherein the liquid test sample is urine.

25. The method of claim 11 wherein the liquid test sample contains about 30 mg/dL or less of protein.

26. The method of claim 11 wherein the liquid test sample contains about 15 mg/dL or less of protein.

27. The method of claim 11 wherein the liquid test sample is urine having a specific gravity of about 1.005 to about 1.030.

28. An analyte detection device for contacting with a liquid test sample to determine the presence or concentration of protein in the liquid test sample, comprising:
  (i) a support strip; and
  (ii) a test pad comprising a carrier matrix having an indicator reagent composition incorporated therein, said indicator reagent composition consisting essentially of:
    (a) an indicator dye capable of interacting with a protein and exhibiting a color transition upon such interaction, said indicator dye being present in an amount of about 0.05 to about 0.6 millimoles per liter of the composition and wherein the indicator dye is selected from the group consisting of 3',3''',5,5''-tetraiodo-3,4,5,6-tetrabromo-phenolsulfophthalein, 3,3'''-diiodo-5,5''',3,4,5,6-hexabromophenolsulfophthalein, and combinations thereof;
    (b) a buffer in an amount of about 250 to about 750 millimoles per liter of the composition wherein the buffer is selected from the group consisting of citric acid, maleic acid, tartaric acid, phthalic acid, sulfosalicyclic acid, succinic acid, malonic acid, their respective alkali metal and ammonium salts and combinations thereof;
    (c) a hydrophobic polymeric compound present in an amount of about 1% to about 8% by weight per milliliter of the composition having the general structural formula:

H—[—A—R$_1$—]$_n$—A—E, wherein A is and PO is an oxypropylene unit, EO is an oxyethylene unit, y is a number in the range of 0 to about 20, z is a number in the range of 0 to about 20, the sum of y+z is a number in the range of about 2 to about 20, and R$_2$ and R$_3$ are selected, independently, from the group consisting of hydrogen, alkyl group, an aralkyl group, and an aryl group;
    R$_1$ is methylene or oxygen;
    n is a number in the range of 1 to about 8; and
    E is hydrogen or methylol when R$_1$ is methylene, or E is hydroxy when R$_1$ is oxygen; and
    (d) a carrier vehicle for said composition.

* * * * *